United States Patent [19]
Khuri-Yakub et al.

[11] Patent Number: 5,257,544
[45] Date of Patent: Nov. 2, 1993

[54] RESONANT FREQUENCY METHOD FOR BEARING BALL INSPECTION

[75] Inventors: B. T. Khuri-Yakub, Palo Alto; Chung-Kao Hsieh, Stanford, both of Calif.

[73] Assignee: The Board of Trustees of the Leland Stanford Junior University, Stanford, Calif.

[21] Appl. No.: 824,001

[22] Filed: Jan. 22, 1992

[51] Int. Cl.⁵ .......................................... G01H 13/00
[52] U.S. Cl. ..................................... 73/579; 73/593; 73/643; 73/657; 73/659
[58] Field of Search ............... 73/579, 593, 596, 598, 73/600, 606, 632, 640, 643, 646, 655, 657, 659

[56] References Cited

U.S. PATENT DOCUMENTS

| | | | |
|---|---|---|---|
| 4,255,971 | 3/1981 | Rosencwaig | 73/606 |
| 4,567,769 | 2/1986 | Barkhoudarian | 73/643 |
| 4,928,527 | 5/1990 | Burger et al. | 73/657 |
| 4,995,259 | 2/1991 | Khuri-Yakub et al. | 73/593 |
| 5,005,417 | 4/1991 | Kawasaki et al. | 73/593 |
| 5,062,296 | 11/1991 | Migliori | 73/659 |

Primary Examiner—Hezron E. Williams
Assistant Examiner—Rose M. Finley
Attorney, Agent, or Firm—Flehr, Hohbach, Test, Albritton & Herbert

[57] ABSTRACT

The present invention provides for an inspection system and method for detecting defects in test objects which includes means for generating expansion inducing energy focused upon the test object at a first location, such expansion being allowed to contract, thereby causing pressure wave within and on the surface of the test object. Such expansion inducing energy may be provided by, for example, a laser beam or ultrasonic energy. At a second location, the amplitudes and phases of the acoustic waves are detected and the resonant frequencies' quality factors are calculated and compared to predetermined quality factor data, such comparison providing information of whether the test object contains a defect. The inspection system and method also includes means for mounting the bearing ball for inspection.

18 Claims, 5 Drawing Sheets

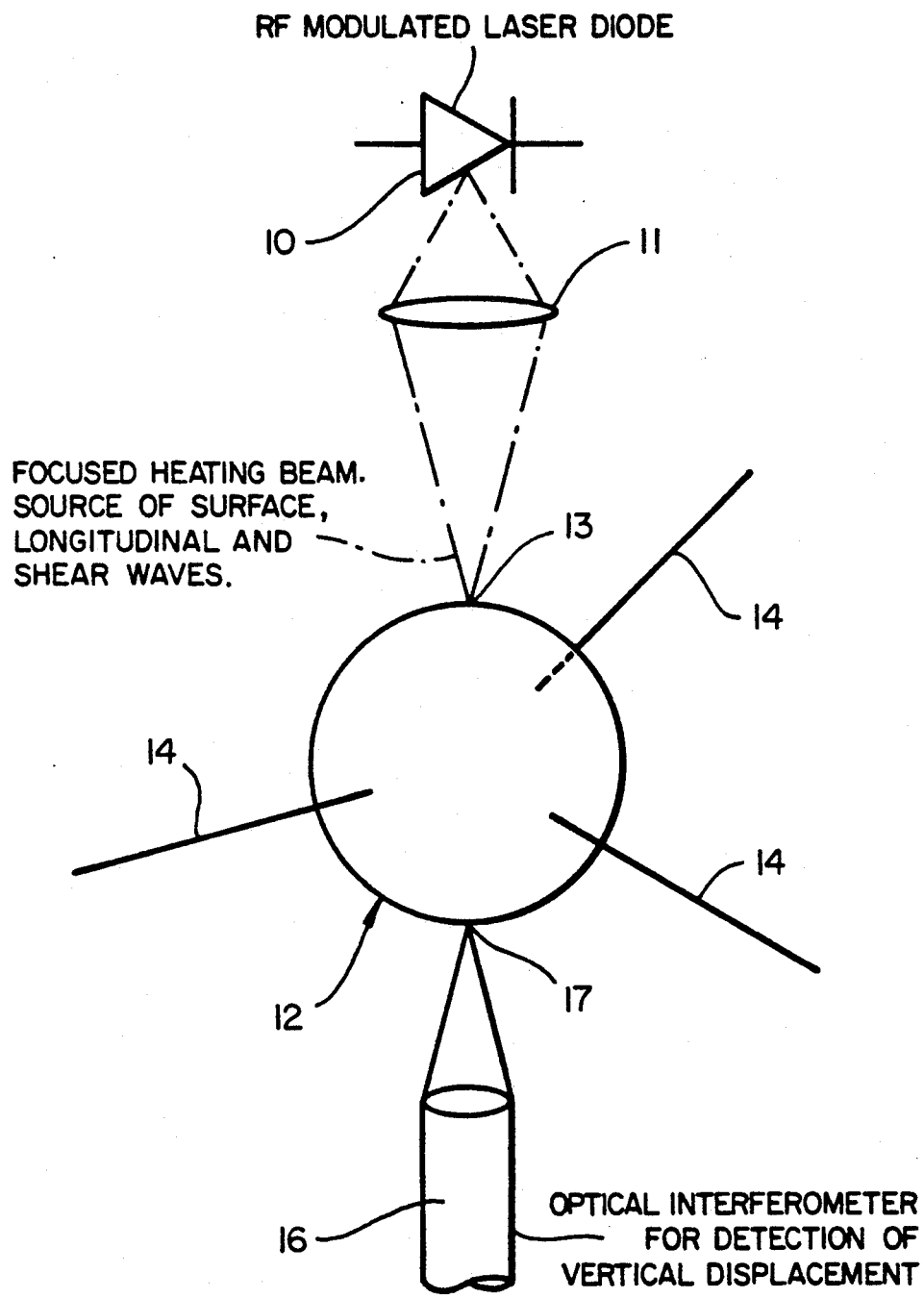
FIG_1

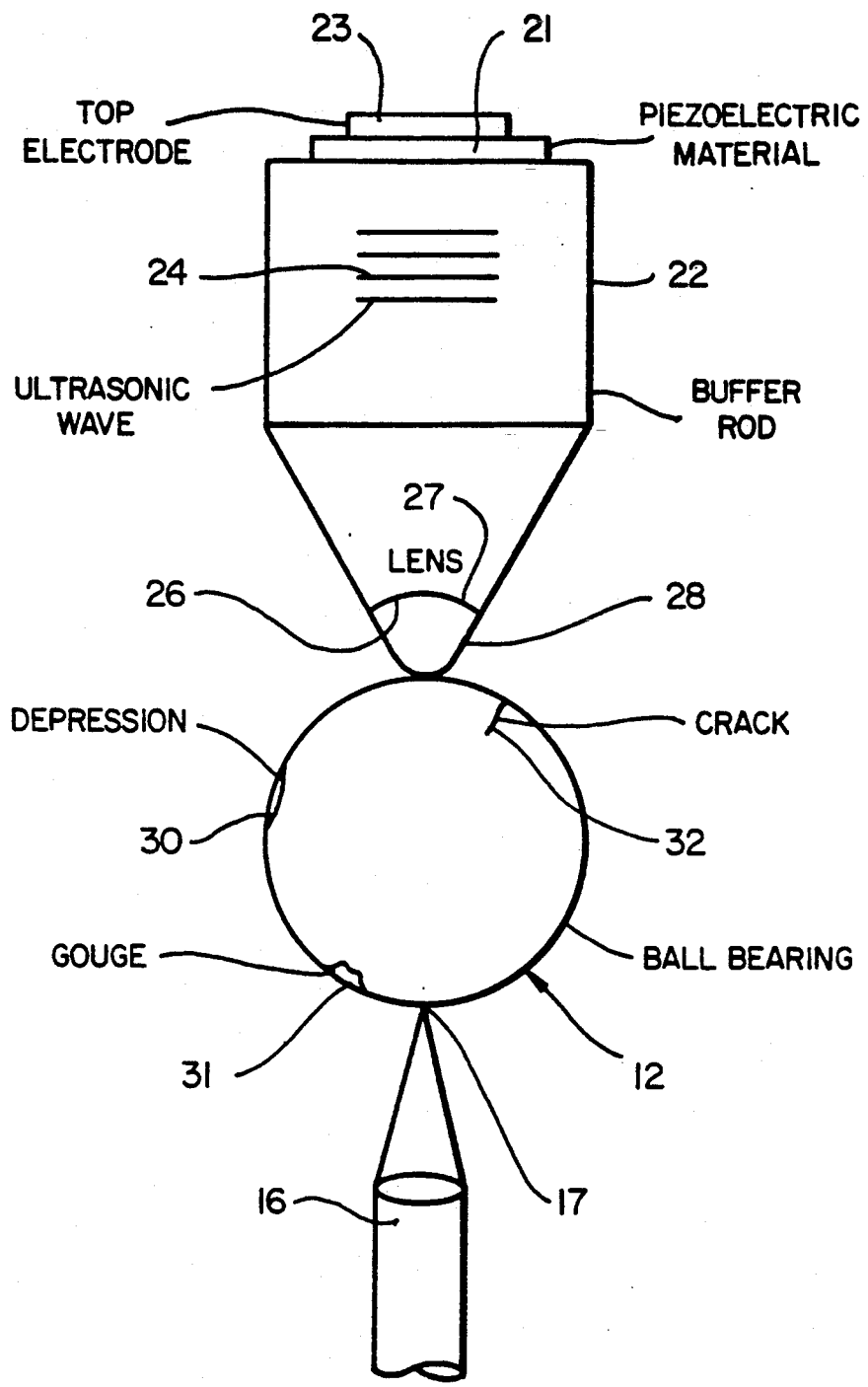
FIG_2

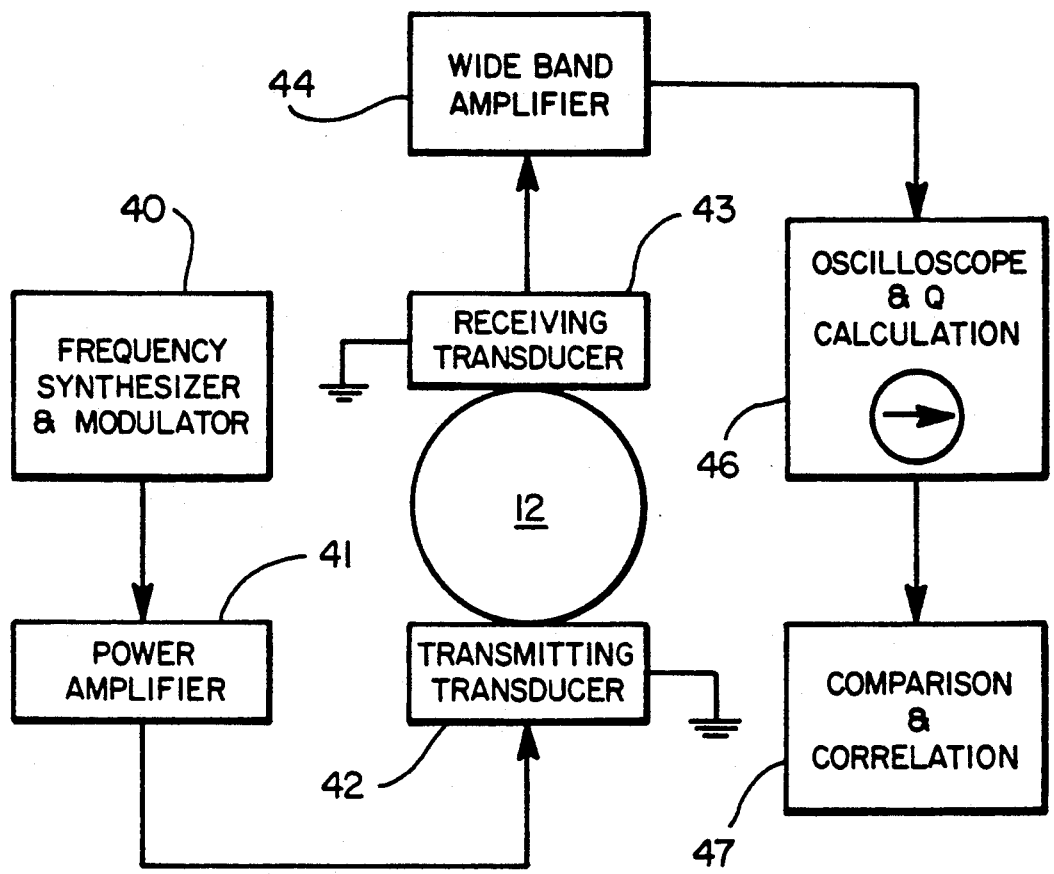
FIG_3

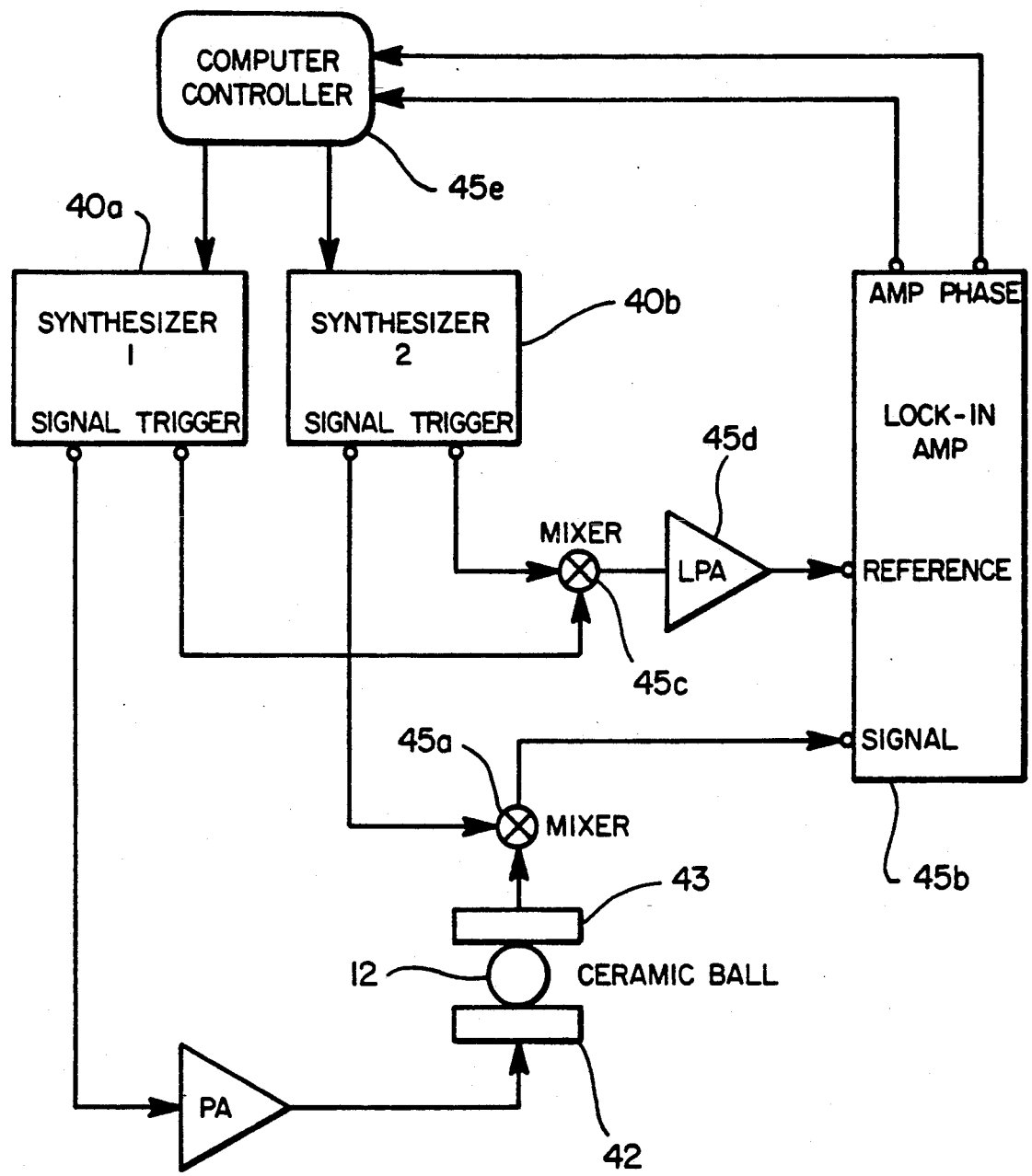
FIG_4

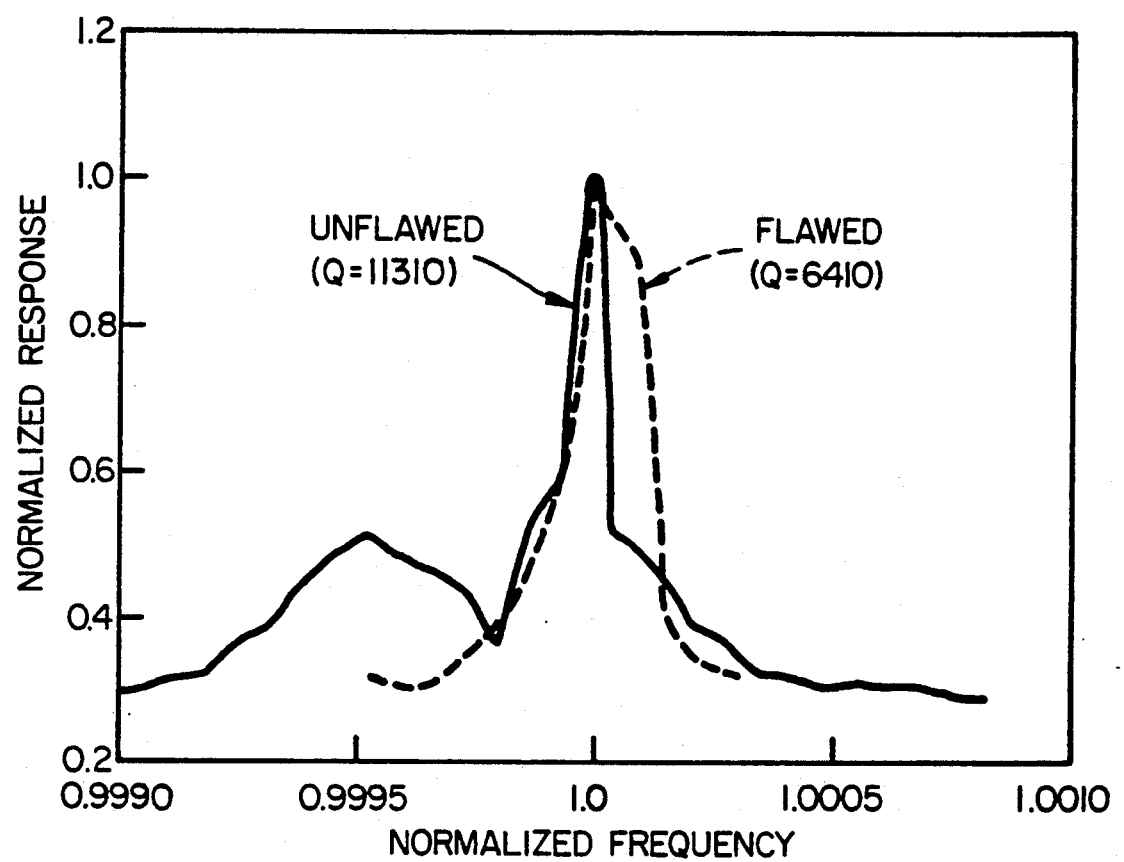
FIG_5

RESONANT FREQUENCY METHOD FOR BEARING BALL INSPECTION

CONTRACT

Department of Energy under Contract No. DE-FG03-84ER45157.

BRIEF DESCRIPTION OF THE INVENTION

This invention relates generally to an inspection system and method for detecting defects in test objects such as bearing balls.

BACKGROUND OF THE INVENTION

Ceramics, such as silicon nitride and silicon carbides, are becoming more widely used by industry in parts that previously were typically made of metals. For example, industry now uses ceramics in the manufacture of bearing balls. Because balls in such bearings are subject to high dynamic stress, and due to the inherent brittleness of ceramics, it is important to inspect each ball for defects, including surface and subsurface cracks or deformities. Stress concentration caused by the existence of surface or subsurface cracks can lead to the total mechanical failure of parts.

It is highly desirable to quickly perform a cursory inspection of a test object for defects. If by that cursory inspection it is determined that the test object is not free of defects, a more detailed inspection of the test object may be performed to determine the type and extent of the defect. In a patent granted to the inventor of the present case, U.S. Pat. No., 4,995,259, therein described is an acoustic microscope surface inspection system for providing detailed defect analysis of a test object.

SUMMARY AND OBJECTS OF THE INVENTION

It is a general object of the present invention to provide an apparatus and method for quickly providing a cursory inspection to test an object for defects.

It is another object of the present invention to use expansion inducing energy focused upon the test object, such as that of a laser beam or ultrasonic energy, to induce acoustic waves on the surface of, and within the test object, having resonant frequencies for which quality factors can be determined.

It is yet another object of the invention to use photo energy or acoustic energy to induce expansion of the test object.

It is a further object of the present invention to provide a microscope system for inspecting a test object which is a sphere, such as a bearing ball.

The foregoing and other objects of the invention are achieved by an inspection system and method which includes means for generating expansion inducing energy and focusing the energy upon the test object at a first location to cause expansion of the object thereby causing acoustic waves within and on the surface of the test object. Such expansion inducing energy may be provided by, for example, a laser beam or ultrasonic energy. At a second location, the phase and amplitude of the acoustic waves are detected by an interferometer. The resonances' quality factors are calculated and compared to predetermined quality factor theoretical calculations to provide an indication of acceptability. The inspection system and method also includes means for mounting the bearing ball for inspection.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 1 schematically shows a photoacoustic inspection system in accordance with the present invention.

FIG. 2 shows an ultrasonic inspection system in accordance with another embodiment of the present invention.

FIG. 3 is a schematic diagram of an ultrasonic system for carrying out the present invention, and an electronic scheme for swept frequency excitation and detection of ultrasonic waves.

FIG. 4 is a schematic diagram of a computer controlled frequency mixing and sampling configuration.

FIG. 5 graphically shows quality factor data extrapolated from data gathered and for two different bearing balls, one with and one without a surface crack.

DESCRIPTION OF THE PREFERRED EMBODIMENT

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the claims.

Turning now to the drawings, wherein like components are designated by like reference numerals, attention is initially directed to FIG. 1. A photoacoustic test object inspection system of the present invention is depicted therein. A laser diode 10 emits light which is focused by lens 11, or other conventional optical components upon test object 12 at a first localized area 13. Preferably the area where the expansion inducing energy is applied to the test object 12 is a small area providing for rapid expansion of the area upon application of energy. Test object 12 in FIG. 1 is of a spherical configuration, however, the method and system disclosed herein is equally applicable to other test object configurations, such as that of a cylinder. In the preferred embodiment, means are provided for positioning the test object 12 for inspection which do not interfere with the testing. A three point support system 14 as schematically shown may serve this purpose.

The light emitted from laser diode 10 upon first location 13 induces expansion of the test object 12. The incident light is at least partially absorbed by the sample, and through expansion, generates surface and bulk waves which propagate on and inside the test object 12.

Means for detection such as an optical interferometer 16, is used to detect the displacement, normal or otherwise, of either or both surface and bulk waves. Optical interferometer 16, in the preferred embodiment, is located at a diametrically opposite point to the first location 13, that is, second location 17. Different types of interferometers may be used for this purpose, including, a Linnik or Mirau configuration.

In another embodiment of the present invention, such as that as shown in FIG. 2, acoustic means are used for generating expansion inducing energy upon test object 12. Acoustic energy may be applied by a transducer with a special cut so that the ultrasonic energy discreetly excites longitudinal waves, shear waves, or surface waves in the test object 12.

A typical acoustic transducer assembly 20 includes a piezoelectric transducer 21 in intimate contact with a buffer rod 22 and an electrode 23 contacting the other surface. The transducer generates ultrasonic waves 24 in response to an electrical signal input. The other end of the buffer rod 22 is made as a sharp tip 28 that contacts the object. The transducer could be made spherical so as to focus the sound on the tip 28.

The test object 12, which in FIG. 2 is a bearing ball, may include three types of defects which may be detected by the present invention. They are a depression 30, a spall 31 and a deep crack 32. Furthermore, defects which are detectable by the present invention may include those which are subsurface such as inhomogeneities in the ceramic material.

Other means for inducing expansion upon a test object may be envisioned, for example, expansion could also be induced by microwaves or by direct heat. Nothing in this disclosure is intended to limit the scope of the present invention.

Another means of inducing acoustic waves in test objects is shown in FIG. 3. Here, two piezoelectric plates are contacted to the test object. Through the contact area between the piezoelectric transducer and the test object, sound is coupled in and out of the test object. At frequencies where the test object responds, strong amplitude waves are excited in the test object and detected by the receiving piezoelectric transducer. In another embodiment (not shown), an acoustic transducer is used to excite the wave while an optical interferometer is used to detect the displacement in the manner shown in FIGS. 1 and 2.

The generating means for generating pulses of expansion inducing energy as shown in FIGS. 1 and 2, that is, the laser diode and the acoustic transducer synthesizer assembly are preferably augmented by frequency modulating means 40 as shown in FIG. 3. It is preferable to include modulating means in conjunction with frequency synthesizer for sweeping through a range of frequencies, thereby inducing acoustic waves within and on the surface of the test object. Typically, at many frequencies, the efficiency of coupling into these modes is very high, and the amplitudes of the detected waves show resonant rise in amplitude. Therefore there may be correlation of the quality factors of a number of resonant frequencies with a variety of predetermined defect data.

FIG. 4 is a schematic diagram of a computer controlled frequency mixing and sampling configuration. A signal from the first synthesizer 40a is sent to the bottom LiNbO3 longitudinal transducer 42, which excites ultrasonic waves on the sphere 12. The top transducer 43, which is similar to the bottom transducer, acts as a receiver. It is positioned to make a Hertzian contact with the sphere. The received signal is mixed with a signal from the second synthesizer 40b with a frequency setting which is 1 KHz lower than that of the first synthesizer 40a. After mixing by mixer 45a, the signal is sent to into a lock-in amplifier 45b where its amplitude and phase are measured. Signals from the trigger output channels of both synthesizers are also mixed by mixer 45c, low passed filtered at 1 KHz by the low pass filter 45d, and then sent into the reference channel of the lock-in amplifier 45b. A computer-controlled system 45e sweeps over the frequency range of interest, therefore providing the ability to measure the resonant frequency spectrum of the sphere. Local maxima in amplitude are used to determine the resonance frequencies of the sphere, whereas the phase data around local amplitude maxima is used to measure the resonance Q's.

The frequency generated by frequency synthesizer 40 is amplified by power amplifier 41 (as shown in FIG. 3), and the amplified generated frequency is imposed upon the test object 12 by transducer 42, such described in detail above with reference to FIGS. 1 and 2. Acoustic waves induced upon test object 12 at the localized area 13 of the test object 12 are detected by receiving transducer 43. Briefly returning to FIGS. 1 and 2, it is shown that the receiving transducer may be an optical interferometer 14. However, any method of detecting the displacement of the surface due to the acoustic waves in the test object 12 is within the scope of the present invention.

FIG. 3 shows the output of the receiving transducer 43 applied to a wide band amplifier 44 which drives oscilloscope 46 where the amplitude data is digitied. The digitized amplitude data, combined with the frequency data, are used together to determine the resonant frequencies. The quality factor, Q, is a measure of the attenuation of a resonant frequency which is defined according to the following approximation for a lightly damped oscillator:

$$Q \approx \frac{\omega_0}{\Delta\omega}$$

where $\Delta\omega$ represents the frequency interval between the points on the amplitude resonance curve that are $1\sqrt{2}=0.707$ of the maximum amplitude.

Using amplitude alone to measure samples with high Q's is time consuming because of the small frequency increment necessary for an accurate measurement. However, because there is a 180° phase change at resonance, there is no need to use small frequency increments to determine amplitude. Instead, by monitoring the phase change, frequency sweeps around resonance avoid the time consuming small frequency increments. The importance of phase measurement is evident for this reason.

At resonance, phase undergoes a change of $\pi$ (radian) and its slope $$\frac{d(\text{phase})}{d(\text{frequency})}$$

is almost constant. The equation for phase near resonance is given by:

$$\theta = \theta_o - \tan^{-1}\frac{(f^2 - f_o^2)Q}{ff_o},$$

where $\theta_o$ is the phase value at resonance, $f_o$ is the resonant frequency, f is the frequency at each sampling point, and Q is the quality factor. Therefore, to determine the resonance Q for a particular mode, the resonant frequency is determined to the desired accuracy from amplitude data, several points around resonance are measured, and a curve is fitted to the measured phase curve according to the above equation. The calculated quality factors are then compared and correlated to a predetermined defect data 47 so it may be determined whether a defect in the test object 12 exists.

FIG. 5 shows a quality factor comparison for indicating whether there is a defect in the test object 12. The abscissa indicates the frequency of the wave and the ordinate indicates the amplitude of the wave. A frequency sweep may start as low as 1 MHz and proceed to frequencies on the order of hundreds of MHz. Accordingly, the resonant frequency data compiled for the graph of FIG. 5 was collected at approximately 14 MHz. The values have all been normalized.

The quality factor of the detected resonant frequency is then correlated to predetermined quality factor data so that a comparison may be effectuated. The solid line 50 is predetermined defect data showing at 14 MHz, the quality factor of what would be a flawless test object 12. The broken line 51 shows the quality factor calculated from the resonant frequency data at 14 MHz in a flawed test object 12. Comparison of the solid line 50 and the broken line 51 provides an indication that the test object is flawed because the solid line 50 and the broken line 51 are not superimposed upon one and other. If there were no flaws detectable at 14 MHz, the lines would be superimposed.

It is unnecessary, of course, to examine the superimposition of the resonant frequency curves upon each other. A simple calculation of the quality factor at a given frequency, and comparison with the quality factor of the predetermined defect data provides an indication of whether a test object 12 is defective. FIG. 5 graphically shows that the solid line 50 has a quality factor of Q=11310 whereas the broken line 51 has a quality factor of Q=6410. The existence of surface cracks typically lowers the surface wave resonance Q's. The discrepancy in the magnitude of these values provides an indication that the test object 12 is defective.

In the general sense, using the resonant frequencies of fundamental modes of spheroidal resonances and torsional resonances, mechanical properties can be calculated. In special cases, pure longitudinal modes can be detected. Furthermore, it has been shown that high modes of spherical resonances are surface acoustic waves. While the present disclosure has been directed to surface acoustic waves, the present invention is also applicable to other types of waves, including longitudinal waves and shear waves.

High-Q modes are more frequency selective and are therefore chosen to calculate the mechanical properties according to the present invention. When the frequency of interest gets higher, the resonance spectrum becomes more complicated as there is an increasing number of closely-spaced higher order resonance modes. In these high order resonance modes, dominating modes are detectable which are nearly equally spaced in the frequency domain. It is believed that these dominating modes are surface wave modes.

In view of the foregoing, it is clear that all of the objectives of the present invention have been met. The general object of the present invention to provide an apparatus and method for quickly providing a cursory inspection of test object for defects has been met. Moreover, the object of the present invention to use an expansion inducing energy focused upon the test object, such as that of a laser beam or ultrasonic energy, to induce acoustic waves within or on the surface of the test object, so as to have resonance at certain frequencies where quality factors can be determined has been met. Furthermore, the object of using photo or acoustic means for inducing expansion have been met. Finally, the object of the present invention to provide a microscope system for inspecting a test object which is of a spherical or cylindrical geometry, such as a ball bearing ball has also been met.

While the invention has been shown and described in what is presently conceived to be the most practical and preferred embodiment of the invention, it will become apparent to those of ordinary skill in the art that many modifications thereof may be made within the scope of the invention, which scope is to be accorded the broadest interpretation of the claims so as to encompass all equivalent structures and devices.

I claim:

1. A method for inspecting a test object for defects comprising the steps of:
    inducing expansion of the test object at a first location on the test object;
    allowing said expansion at said first location to induce acoustic waves;
    detecting, at a second location on the test object, the amplitude and phase of said acoustic waves;
    determining resonant frequencies of said test object from said amplitude and said phase of said acoustic waves;
    calculating quality factors of said resonant frequencies;
    correlating said quality factors to predetermined defect data; and
    indicating whether the test object contains defects according to said correlation step.

2. A method as recited in claim 1 wherein inducing expansion of the test object comprises the step of focusing a laser beam at a first location on the test object.

3. A method as recited in claim 2 wherein said laser beam is frequency modulated.

4. A method as recited in claim 1 wherein inducing expansion of the test object comprises the step of focusing ultrasonic energy at a first location on the test object.

5. A method as recited in claim 4 wherein said ultrasonic energy is frequency modulated.

6. A method as recited in claim 4 wherein said ultrasonic energy discreetly excites longitudinal waves, shear waves and surface waves.

7. A method as recited in claim 1 wherein the test object is a sphere and means are provided for positioning the test object for said inspection.

8. A method as recited in claim 1 wherein the test object is a cylinder and means are provided for positioning the test object for said inspection.

9. A method for inspecting a test object for defects, comprising the steps of:
    focusing expansion inducing energy at a first limited area on said test object, thereby inducing expansion of said test object at said first location;
    allowing said first location to contract from said expansion, such that wave action is excited within and on the surface of the test object, thereby creating waves;
    determining displacement data by detecting, at a second location on the test object, displacement of said waves caused by said defects, said displacement data comprising amplitude and phase of said waves;
    determining resonant frequencies of said test object from said detected displacement data;

calculating quality factors of said resonant frequencies;

comparing said quality factors to predetermined defect data; and indicating whether the test object contains defects according to said comparing step.

10. A method as recited in claim 9 wherein said expansion inducing energy comprises a frequency modulated laser beam.

11. A method as recited in claim 9 wherein said expansion inducing energy comprises frequency modulated ultrasonic energy.

12. A method as recited in claim 9 wherein the test object is a sphere and means are provided for positioning the test object for said inspection.

13. A method as recited in claim 9 wherein the test object is a cylinder and means are provided for positioning the test object for said inspection.

14. A photoacoustic test object inspection system for detecting defects in a test object, comprising:

generating means for pulse generating expansion inducing energy, such causing expansion of said test object;

directing means for directing said energy on to the surface of the test object at a first location wherein wave action may be excited within and on the surface of the test object, thereby creating acoustic waves;

detecting means at a second location for detecting the amplitude and phase of normal displacement of said acoustic waves;

determining resonant frequencies of said test object from said amplitude and said phase of said acoustic waves;

calculation means for calculating quality factors of said resonant frequencies;

correlation means for correlating said quality factors to predetermined defect data; and indication means for indicating the correlation between said quality factor and said predetermined defect data.

15. A system as recited in claim 14 wherein said generating means generates a laser beam.

16. A system as recited in claim 14 wherein said generating means generates ultrasonic energy.

17. A system as recited in claim 14 further comprising modulating means for modulating the frequency of said energy.

18. A system as recited in claim 14 wherein the test object is a sphere and means are provided for positioning the test object for said inspection.

* * * * *